(12) United States Patent
Blank

(10) Patent No.: US 11,684,739 B2
(45) Date of Patent: Jun. 27, 2023

(54) MULTIPLE BEAK ENDOTRACHEAL DEVICE AND RELATED METHODS THEREOF

(71) Applicant: University of Virginia Patent Foundation, Charlottesville, VA (US)

(72) Inventor: Randal S. Blank, Charlottesville, VA (US)

(73) Assignee: UNIVERSITY OF VIRGINIA PATENT FOUNDATION, Charlottesville, VA (US)

( * ) Notice: Subject to any disclaimer, the term of this patent is extended or adjusted under 35 U.S.C. 154(b) by 1117 days.

(21) Appl. No.: 16/316,712

(22) PCT Filed: Jul. 13, 2017

(86) PCT No.: PCT/US2017/041909
§ 371 (c)(1),
(2) Date: Jan. 10, 2019

(87) PCT Pub. No.: WO2018/013795
PCT Pub. Date: Jan. 18, 2018

(65) Prior Publication Data
US 2019/0240434 A1 Aug. 8, 2019

Related U.S. Application Data

(60) Provisional application No. 62/362,324, filed on Jul. 14, 2016.

(51) Int. Cl.
*A61M 16/04* (2006.01)
*A61B 1/00* (2006.01)
*A61M 25/00* (2006.01)

(52) U.S. Cl.
CPC ..... *A61M 16/0486* (2014.02); *A61B 1/00135* (2013.01); *A61M 16/0404* (2014.02);
(Continued)

(58) Field of Classification Search
CPC ............. A61M 16/04; A61M 16/0402; A61M 16/0404; A61M 16/0418; A61M 16/0427;
(Continued)

(56) References Cited

U.S. PATENT DOCUMENTS 2,862,498 A * 12/1958 Weekes ............. A61M 16/0463
128/207.14
3,169,529 A * 2/1965 Koenig ............. A61M 16/0488
128/207.14
(Continued)

FOREIGN PATENT DOCUMENTS

CN 202236751 U * 5/2012
JP 2010178888 A * 8/2010
WO WO-2017010201 A1 * 1/2017

OTHER PUBLICATIONS

Collins, Stephen R., et al., "Lung Isolation in the Patient with a Difficult Airway", Anesthesia & Analgesia, Jun. 2018, pp. 1968-1978, vol. 126, No. 6.
(Continued)

*Primary Examiner* — Kathryn E Ditmer
(74) *Attorney, Agent, or Firm* — Robert J. Decker

(57) ABSTRACT

A device and method that reduces impingement upon fragile airway structures and improves the performance and safety associated with endotracheal devices and related intubation procedures. The endotracheal device includes a lumen such that one end of the lumen includes an anterior beak that includes a distal tip of the anterior beak and a posterior beak having a distal tip of the posterior beak.

24 Claims, 8 Drawing Sheets

(52) U.S. Cl.
CPC .... *A61M 16/0459* (2014.02); *A61M 16/0484* (2014.02); *A61M 25/0026* (2013.01)

(58) Field of Classification Search
CPC .......... A61M 16/0429; A61M 16/0431; A61M 16/0475; A61M 16/0484; A61M 16/0486; A61M 25/0026; A61M 29/00; A61B 1/00135; A61F 13/26; A61F 13/266
USPC ....................................................... D24/141
See application file for complete search history.

(56) References Cited

U.S. PATENT DOCUMENTS

| | | | | |
|---|---|---|---|---|
| 4,157,709 | A * | 6/1979 | Schuster | A61B 10/0291 600/572 |
| 5,339,805 | A | 8/1994 | Parker | |
| 5,743,254 | A | 4/1998 | Parker | |
| 5,752,970 | A * | 5/1998 | Yoon | A61B 17/3498 604/167.03 |
| 5,845,634 | A | 12/1998 | Parker | |
| 5,873,362 | A * | 2/1999 | Parker | A61M 16/0418 128/207.14 |
| 6,095,144 | A * | 8/2000 | Pagan | A61M 16/0418 128/207.14 |
| 6,358,223 | B1 * | 3/2002 | Mackay | A61F 13/26 604/15 |
| 6,443,156 | B1 * | 9/2002 | Niklason | A61M 16/04 128/207.14 |
| 6,568,393 | B2 | 5/2003 | Christopher | |
| 6,609,521 | B1 | 8/2003 | Belani et al. | |
| 6,672,305 | B2 | 1/2004 | Parker | |
| 6,698,428 | B2 | 3/2004 | Brain | |
| 6,918,391 | B1 | 7/2005 | Moore | |
| 6,923,176 | B2 * | 8/2005 | Ranzinger | A61M 16/04 128/207.14 |
| 7,174,889 | B2 | 2/2007 | Boedeker et al. | |
| 2001/0013344 | A1 | 8/2001 | Chou | A61M 16/0495 128/200.26 |
| 2002/0179091 | A1 * | 12/2002 | Christopher | A61M 16/04 128/207.15 |
| 2004/0020491 | A1 | 2/2004 | Fortuna | |
| 2006/0020347 | A1 | 1/2006 | Barrett et al. | |
| 2008/0216839 | A1 * | 9/2008 | Rutter | A61M 16/0418 128/207.14 |
| 2010/0016780 | A1 * | 1/2010 | VanDenBogart | A61F 13/26 604/15 |
| 2010/0113916 | A1 | 5/2010 | Kumar | |
| 2010/0164139 | A1 * | 7/2010 | LeMay | A61F 13/26 264/296 |
| 2010/0224186 | A1 | 9/2010 | Uesugi | |
| 2013/0079755 | A1 * | 3/2013 | House | A61M 25/0017 604/544 |
| 2014/0007882 | A1 * | 1/2014 | Wu | A61M 16/0459 128/207.15 |
| 2014/0323806 | A1 * | 10/2014 | Brain | A61B 1/00154 600/114 |
| 2015/0297196 | A1 * | 10/2015 | Ching | A61B 10/0045 600/572 |
| 2016/0192829 | A1 * | 7/2016 | Poulsen | A61M 16/0816 600/115 |

OTHER PUBLICATIONS

Gamez, Ryan, et al., "A Simulator Study of Tube Exchange with Three Different Designs of Double-Lumen Tubes", Anesthesia & Analgesia, Aug. 2014, pp. 449-453, vol. 119, No. 2.

Johnson, Dana M., et al., "Endoscopic Study of Mechanism of Failure of Endotracheal Tube Advancement into the Trachea during Awake Fiberoptic Orotracheal Intubation", Anesthesiology, May 2005, pp. 910-914, vol. 102, No. 5.

Knoll, Heike, et al., "Airway Injuries after One-lung Ventilation: A Comparison between Double-lumen Tube and Endobronchial Blocker", Anesthesiology, Sep. 2006, pp. 471-477, vol. 105, No. 3.

Lee, Jung Seog, et al., "Comparison of a Silicon Double-Lumen Endobronchial Tube (Silbroncho®) with a Polyvinyl Chloride Tube (Broncho-Cath®) in Right-Side Thoracic Surgery", Korean Journal of Anesthesiology, May 2005, pp. 509-513, vol. 48, No. 5 (English abstract).

Liu, Shiqing, et al., "Airway Rupture Caused by Double-Lumen Tubes: A Review of 187 Cases", Anesthesia & Analgesia, Nov. 2020, pp. 1485-1490, vol. 131, No. 5.

Maktabi, Mazen, A., et al., "Laryngeal Trauma during Awake Fiberoptic Intubation", Anesthesia & Analgesia, Oct. 2002, pp. 1112-1114, vol. 95, No. 4.

McLean, Sheron, et al., "Airway Exchange Failure and Complications with the Use of the Cook Airway Exchange Catheter®: A Single Center Cohort Study of 1177 Patients", Anesthesia & Analgesia, Dec. 2013, pp. 1325-1327, vol. 117, No. 6.

Orlewicz, Marc S., et al., "DoubleLumen Endotracheal Tube Placement", Medscape Reference Drugs, Diseases & Procedures, updated Feb. 29, 2016, 6 pages.

* cited by examiner

LAYRNGOSCOPIC VIEW DEPICTION

MULTIPLE BEAK ENDOTRACHEAL DEVICE AND RELATED METHODS THEREOF

RELATED APPLICATIONS

The present application is a national stage filing of International Application No. PCT/US2017/041909, filed Jul. 13, 2017, which claims benefit of priority under 35 U.S.C § 119 (e) from U.S. Provisional Application Ser. No. 62/362,324, filed Jul. 14, 2016, entitled "Easy Pass Double Lumen Endotracheal Tube and Related Methods Thereof"; the disclosures of which are hereby incorporated by reference herein in their entirety.

FIELD OF INVENTION

The present disclosure relates generally to endotracheal intubation devices, and more particularly an endotracheal device that consists of two opposing beaks that decrease the potential impingement upon fragile airway structures and improves the performance and safety associated with endotracheal devices and related procedures.

BACKGROUND

Endotracheal intubation is a critical component of respiratory support for patients experiencing respiratory failure and for those undergoing a wide variety of elective and emergency procedures. Single lumen endotracheal tubes are routinely used to provide a secure airway in patients requiring ventilatory support for critical care and/or surgical procedures. Double lumen endotracheal tubes are used a) to provide lung protection in patients with certain unilateral lung conditions which threaten soilage of a remaining intact lung, b) to provide adequate ventilation in patients with severe unilateral lung disease, and c) to achieve lung isolation and one lung ventilation in patients undergoing a variety of intrathoracic surgical procedures.

The placement and correct positioning of endotracheal tubes, particularly double lumen endotracheal tubes can be difficult and is intrinsically hazardous, particularly in a number of clinical scenarios, including abnormal upper or lower airway anatomy. The risk of failure to intubate under these scenarios places the patient at elevated risk of hypoxemia and hypercarbia which may be severe—leading to cardiac arrest. The risk of intubation related injury in difficult scenarios often manifests as sore throat or hoarseness and may result in severe glottic or tracheobronchial injury. Such injuries can be devastating, leading to the acute need for major surgical intervention, cardiovascular compromise, and even death.

The placement of both single and double lumen endotracheal tubes can be facilitated with the use of a number of airway management adjuncts, including introducing devices—devices specifically designed for the endotracheal tubes to be passed over and thus to facilitate endotracheal intubation. These introducing devices may include, but not limited thereto, fiberoptic bronchoscopes, airway exchange catheters, endotracheal tube introducers, and obturator/wire devices. When these introducing devices are used to facilitate intubation, the introducing device typically impinges upon the posterior aspect of the glottis—most commonly the posterior aspect of the vocal cords, the arytenoid, or the interarytenoid tissue. The presence of a single beak has been shown to increase success of intubation under these conditions, but often requires significant rotation of the tube, since a single beak may not adequately decrease the gap between an introducing device and the posterior wall of the endotracheal tube.

The above problems are limitations that are greatly magnified with the attempted placement of a double lumen endotracheal tube. These double lumen endotracheal tubes are larger, stiffer, less flexible, and must be placed deeper within the tracheobronchial tree. Thus, they are more difficult to place, requiring more experience and expertise; placement fails more frequently and they are much more likely to cause mild, moderate, and severe airway injuries. The first consistent obstacle to placement is the glottis itself. The tube must be introduced through and past the vocal cords. The large stiff blunt tip of this double lumen endotracheal tube frequently makes this maneuver difficult and thus increases the incidence of failure and risk. If the endotracheal tube is to be passed over an introducing device (as enumerated above), this risk is greatly magnified, as is the risk of failure. Currently, no single beaked (as well any double beaked) double lumen endotracheal tubes are available. Even if such a single beak double lumen endotracheal tube was available, it is unlikely to greatly improve passage through the glottis, since impingement would still occur posteriorly.

Once a double lumen endotracheal tube successfully traverses the glottis, it has to be traverse the entire length of the trachea and pass into the desired mainstem bronchus. Potential sites of impingement, for example, are 1) the immediate subglottic trachea—at the level of cricoid ring, 2) the carina, and 3) any deviation, compression, or other abnormality in the tracheobronchial tree (which may be a common condition in patients presenting for thoracic surgical procedures).

Moreover, the conventional double lumen tube, because it often has to be vigorously manipulated to pass the subglottic trachea, is most likely to injure the susceptible posterior tracheal wall, which is not supported by cartilaginous rings.

There is a need in the art for a device that reduces impingement upon fragile airway structures and improves the performance and safety associated with endotracheal devices and related procedures.

SUMMARY OF EXEMPLARY EMBODIMENTS OF THE INVENTION

An aspect of an embodiment of the present invention provides, but not limited thereto, an endotracheal device that may include: a lumen having an inner diameter and central axis running longitudinally along the length of the lumen; the lumen having a proximal portion and a distal portion opposite the proximal portion; and the distal portion having an anterior beak that includes a distal tip of the anterior beak and a posterior beak having a distal tip of the posterior beak. In an embodiment the distal tip of the anterior beak longitudinally may extend distally a predetermined distance from the distal tip of the posterior beak so as to define a longitudinal beak offset. In an embodiment the distal tip of the anterior beak is laterally inward a predetermined distance from the distal tip of the posterior beak so as to define a lateral-inward beak offset. In an embodiment the distal tip of the posterior beak is laterally inward a predetermined distance from the distal tip of the anterior beak so as to define a lateral-inward beak offset. One or both of the anterior beak and posterior beak may be directed, aligned, and curved laterally inward.

An aspect of an embodiment provides a device (and related method) that reduces impingement upon fragile airway structures and improves the performance and safety associated with endotracheal devices and related intubation procedures.

An aspect of an embodiment of the double beak lumen of an endotracheal device shall, but not limited thereto, improve passage at each level of the related anatomy and reduce the risks of injury as follows:

a) First, because tip of the endotracheal device 21 has both an anterior beak 41 and posterior beak 51, passage through the glottis 153 will be facilitated, with or without an introducing device. The anterior beak 41 and the posterior beak 51 of the lumen 31 of the endotracheal device 21 will serve to minimize the gap between the anterior luminal wall and posterior luminal wall of the endotracheal tube and any introducing device and to reduce impingement on both the anterior and posterior glottis structures during passage. The posterior beak may be particularly important at this glottis level or thereabout.

b) Secondly, the anterior beak 41 of the lumen (with or without an introducing device) of the endotracheal device 21 will facilitate passage in the immediate subglottic trachea 135, a common site of impingement anteriorly.

c) Third, both the anterior beak 41 and posterior beak 51 of the endotracheal device 21 will reduce friction during passage down the trachea 3 and reduce the risk of injury to the fragile posterior tracheal wall 137.

d) Fourth, both the anterior beak 41 and posterior beak 51 of the lumen 31 of the endotracheal device 21 will improve passage through areas of deviation or compression by reducing impingement of an otherwise blunt stiff tip.

e) Finally, both the anterior beak 41 and posterior beak 51 of the lumen 31 of the endotracheal device 21 (particularly the posterior beak 51) will facilitate passage into the mainstem bronchus and reduce impingement on and injury to the tracheal carina 7.

The above exemplary enumerated aspects, attributes, features and advantages of the double beak endotracheal device shall be applicable for all levels of the applicable anatomy of tracheobronchial tree (e.g., larynx, trachea 3, primary bronchi, tertiary bronchi, and secondary bronchi).

An aspect of an embodiment of the double beak lumen shall, but not limited thereto, improve passage at each level of the larynx, trachea, primary bronchi, tertiary bronchi, and secondary bronchi and reduce the risks of injury of various potential sites of impingement that may include, for example as follows 1) the immediate subglottic trachea 135—at the level of cricoid ring, 2) the carina 7, and 3) any deviation, compression, or other abnormality in the tracheobronchial tree (which may be a common condition in patients presenting for thoracic surgical procedures).

It should be appreciated that any of the components or modules referred to with regards to any of the present invention embodiments discussed herein, may be integrally or separately formed with one another. Further, redundant functions or structures of the components or modules may be implemented. Moreover, the various components may be communicated locally and/or remotely with any user/clinician/patient or machine/system/computer/processor. Moreover, the various components may be in communication via wireless and/or hardwire or other desirable and available communication means, systems and hardware. Moreover, various components and modules may be substituted with other modules or components that provide similar functions.

It should be appreciated that the device and related components discussed herein may take on all shapes along the entire continual geometric spectrum of manipulation of x, y and z planes to provide and meet the anatomical, environmental, and structural demands and operational requirements. Moreover, locations and alignments of the various components may vary as desired or required.

It should be appreciated that various sizes, dimensions, contours, rigidity, shapes, flexibility and materials of any of the components or portions of components in the various embodiments discussed throughout may be varied and utilized as desired or required.

It should be appreciated that while some dimensions are provided on the aforementioned figures, the device may constitute various sizes, dimensions, contours, rigidity, shapes, flexibility and materials as it pertains to the components or portions of components of the device, and therefore may be varied and utilized as desired or required.

Although example embodiments of the present disclosure are explained in detail herein, it is to be understood that other embodiments are contemplated. Accordingly, it is not intended that the present disclosure be limited in its scope to the details of construction and arrangement of components set forth in the following description or illustrated in the drawings. The present disclosure is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the present disclosure. Similarly, it is also to be understood that the mention of one or more components in a device or system does not preclude the presence of additional components or intervening components between those components expressly identified.

As discussed herein, a "subject" may be any applicable human, animal, or other organism, living or dead, or other biological or molecular structure or chemical environment, and may relate to particular components of the subject, for instance specific tissues or fluids of a subject (e.g., human tissue in a particular area of the body of a living subject), which may be in a particular location of the subject, referred to herein as an "area of interest" or a "region of interest."

Some references, which may include various patents, patent applications, and publications, are cited in a reference list and discussed in the disclosure provided herein. The citation and/or discussion of such references is provided merely to clarify the description of the present disclosure and is not an admission that any such reference is "prior art" to any aspects of the present disclosure described herein. In terms of notation, "[n]" corresponds to the $n^{th}$ reference in the list. All references cited and discussed in this specification are incorporated herein by reference in their entireties and to the same extent as if each reference was individually incorporated by reference.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 10% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, 4.24, and 5). Similarly, numerical ranges recited herein by endpoints include subranges subsumed within that range (e.g. 1 to 5 includes 1-1.5, 1.5-2, 2-2.75, 2.75-3, 3-3.90, 3.90-4, 4-4.24, 4.24-5, 2-5, 3-5, 1-4, and 2-4). It is also to be understood that all numbers and fractions thereof are presumed to be modified by the term "about."

The invention itself, together with further objects and attendant advantages, will best be understood by reference to the following detailed description, taken in conjunction with the accompanying drawings.

BRIEF DESCRIPTION OF THE DRAWINGS

The foregoing and other objects, features and advantages of the present invention, as well as the invention itself, will be more fully understood from the following description of preferred embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

DETAILED DESCRIPTION OF EXEMPLARY EMBODIMENTS

Figure 1:
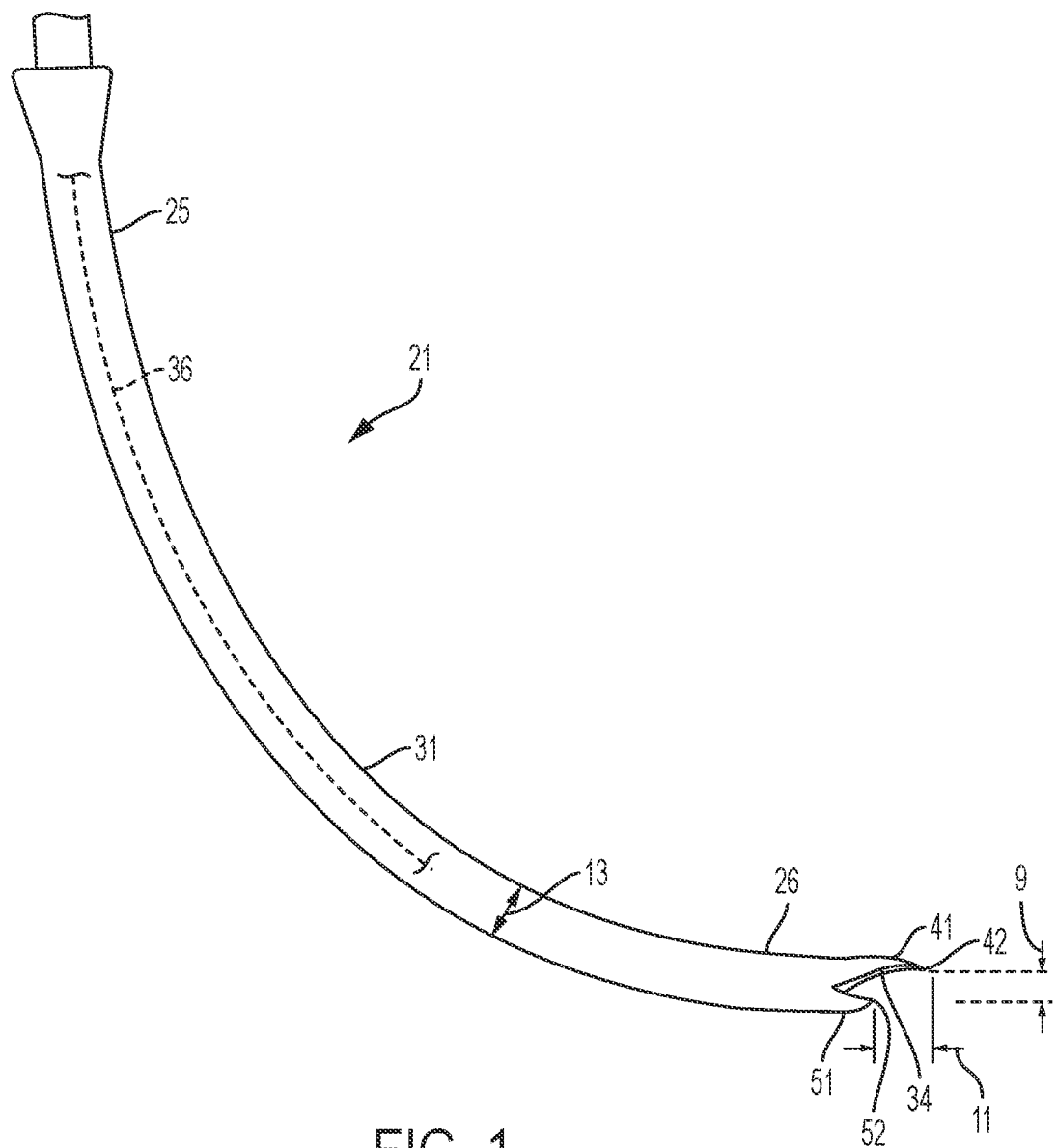
FIG. 1 schematically illustrates a single lumen endotracheal device.
Figure 3:
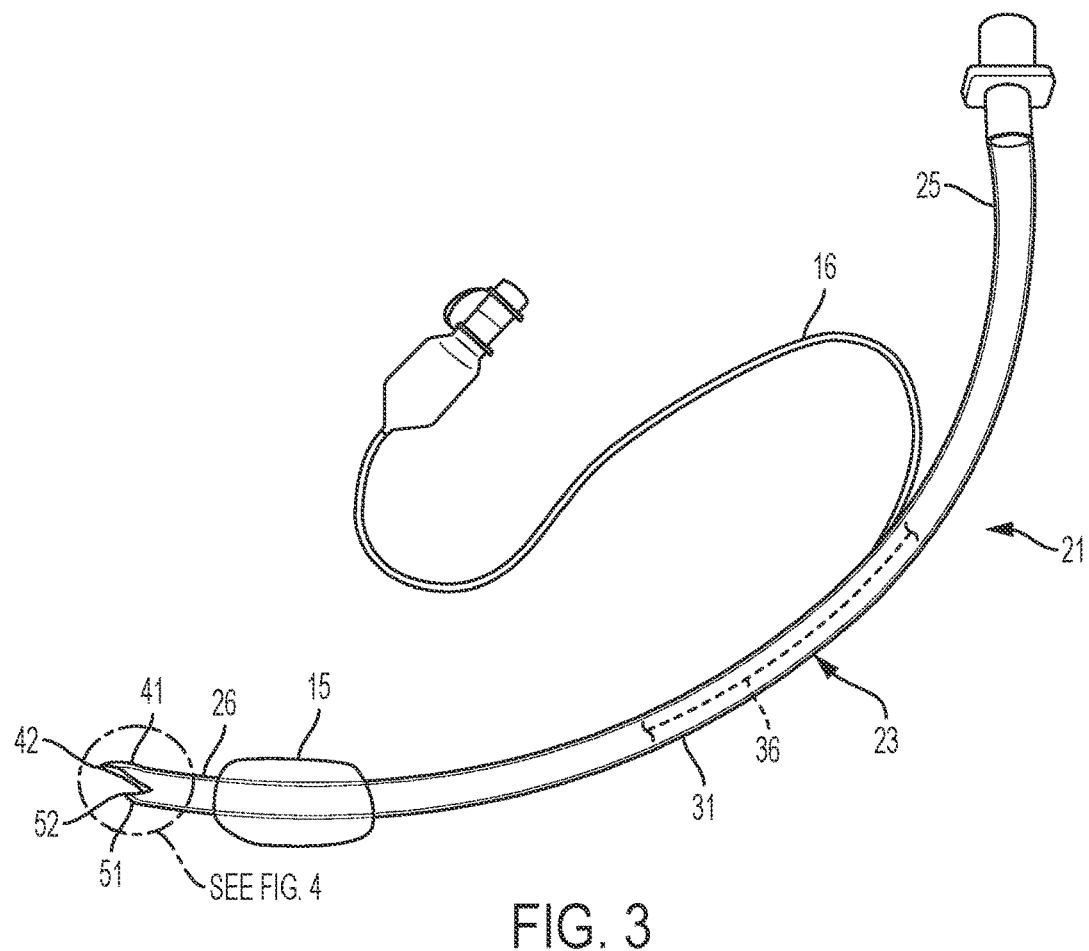
FIG. 3 schematically illustrates a single lumen endotracheal device.

FIGS. 1 and 3 schematically illustrates an embodiment of an endotracheal device 21 that may include a lumen 31 such as a bronchial lumen having a central longitudinal axis 36, an inner diameter 13 of the lumen 31, a proximal portion 25, and a distal portion 26, wherein the distal portion 26 includes an anterior beak 41 having a distal tip 42 of the anterior beak 41 and a posterior beak 51 having a distal tip 52 of the posterior beak 51, which defines the lumen aperture 34. The distal tip 42 of the anterior beak 41 may longitudinally extend distally a predetermined distance from the distal tip 52 of said posterior beak 51 so as to define a longitudinal beak offset 11. Moreover, the distal tip 42 of the anterior beak 41 may be laterally inward a predetermined distance from the distal tip 52 of said posterior beak 51 so as to define a lateral-inward beak offset 9 (shown in FIGS. 1 and 4). Alternatively, the distal tip 42 of the anterior beak 41 may be laterally outward (although not specifically depicted in the Figures) a predetermined distance from the distal tip 52 of said posterior beak 51 so as to define a lateral-outward beak offset. For instance, although not shown, the distal tip 42 of the anterior beak 41 may extend outward beyond the wall of the lumen 31 and/or the distal tip 52 of said posterior beak 51 may extend outward beyond the wall of the lumen 31. This may be applicable to various embodiments disclosed herein.

Figure 2:
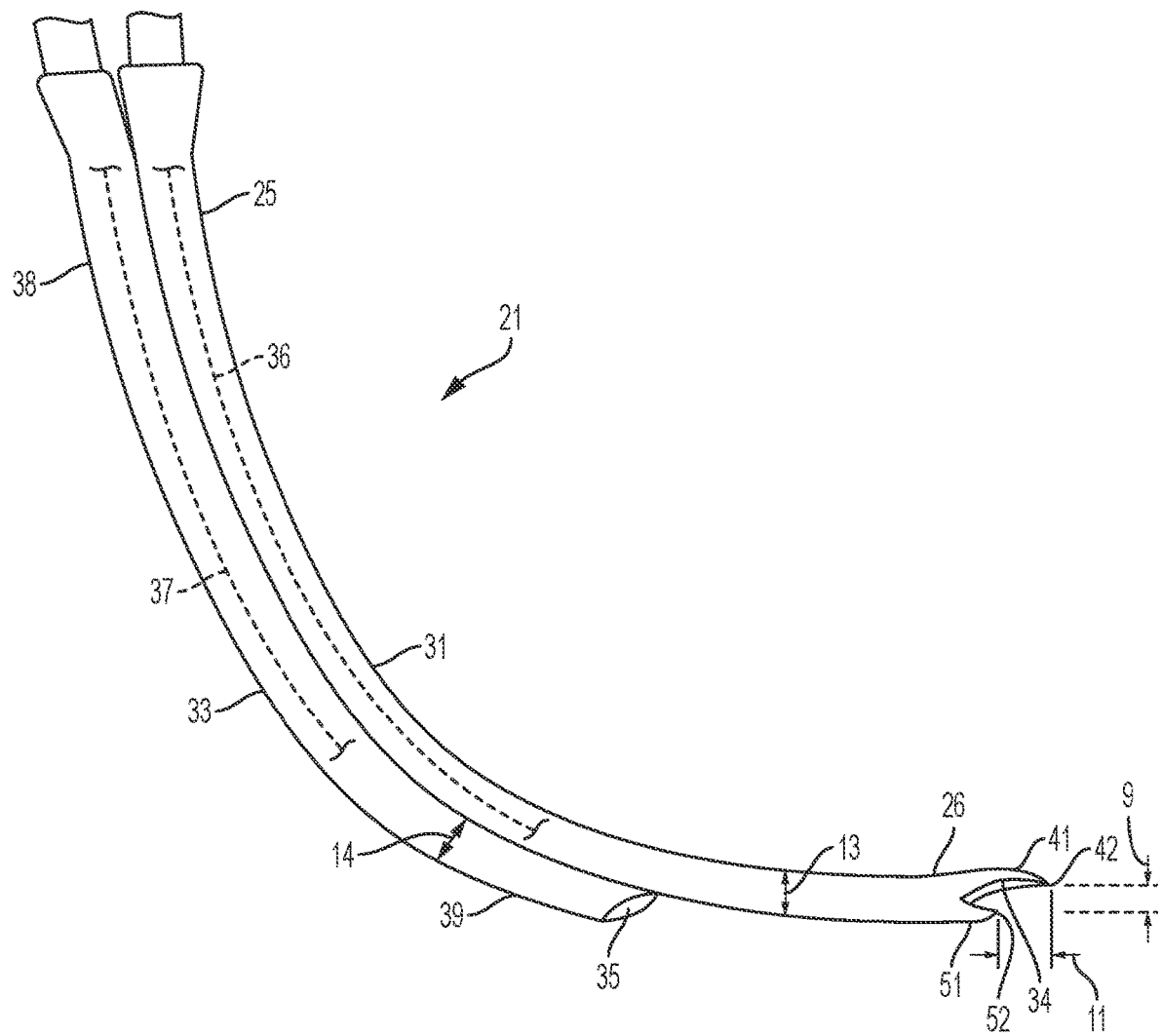
FIG. 2 schematically illustrates a double lumen endotracheal device.
Figure 5:
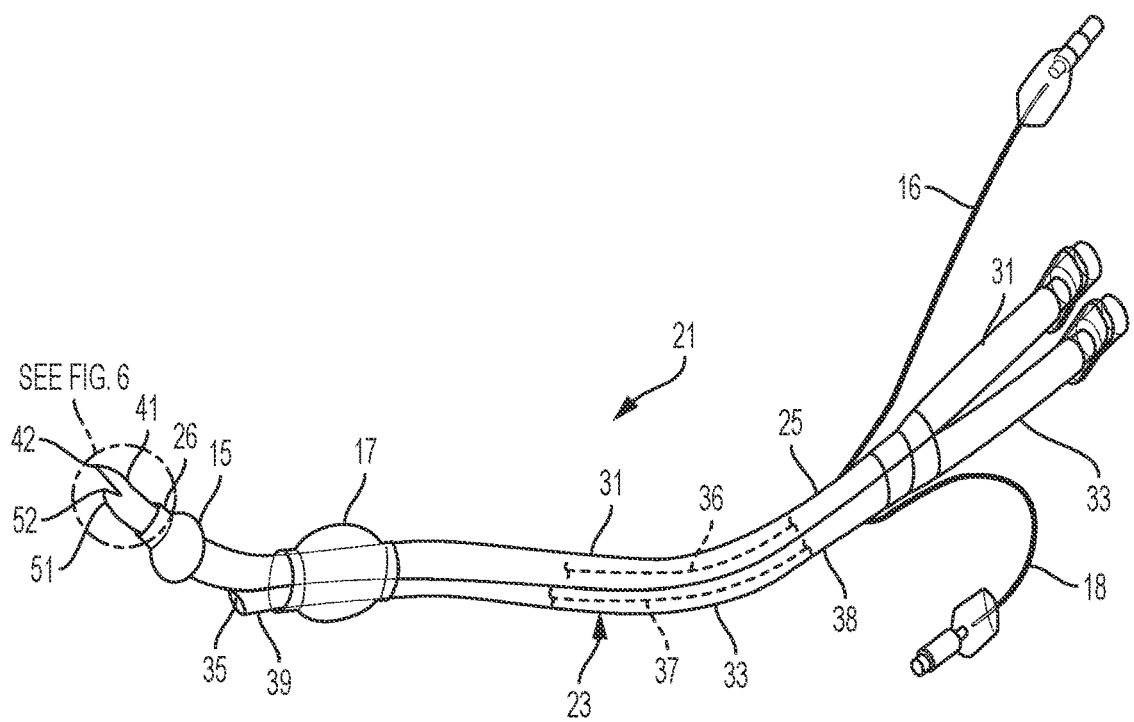
FIG. 5 schematically illustrates a double lumen endotracheal device.

FIGS. 2 and 5 schematically illustrates an embodiment of an endotracheal device 21 that may include a lumen 31 such as a bronchial lumen having a central longitudinal axis 36, an inner diameter 13 of the lumen 31, a proximal portion 25, and a distal portion 26, wherein the distal portion 26 includes an anterior beak 41 having a distal tip 42 of the anterior beak 41 and a posterior beak 51 having a distal tip 52 of the posterior beak 51, which defines the lumen aperture 34. The distal tip 42 of the anterior beak 41 may longitudinally extend distally a predetermined distance from the distal tip 52 of said posterior beak 51 so as to define a longitudinal beak offset 11. Moreover, the distal tip 42 of the anterior beak 41 may be laterally inward a predetermined distance from the distal tip 52 of said posterior beak 51 so as to define a lateral-inward beak offset 9 (shown in FIGS. 2 and 6). Alternatively, the distal tip 42 of the anterior beak 41 may be laterally outward a predetermined distance from the distal tip 52 of said posterior beak 51 so as to define a lateral-outward beak offset (although not specifically depicted in the Figures). For instance, although not shown, the distal tip 42 of the anterior beak 41 may extend outward beyond the wall of the lumen 31 and/or the distal tip 52 of said posterior beak 51 may extend outward beyond the wall of the lumen 31. This may be applicable to various embodiments disclosed herein.

Still referring FIGS. 2 and 5, the endotracheal device 21 may include a second lumen 33 such as a tracheal lumen having a central longitudinal axis 37, an inner diameter 14 of the second lumen 33, a proximal portion 38, and a distal portion 39, which includes an aperture 35 of the lumen.

Figure 7:
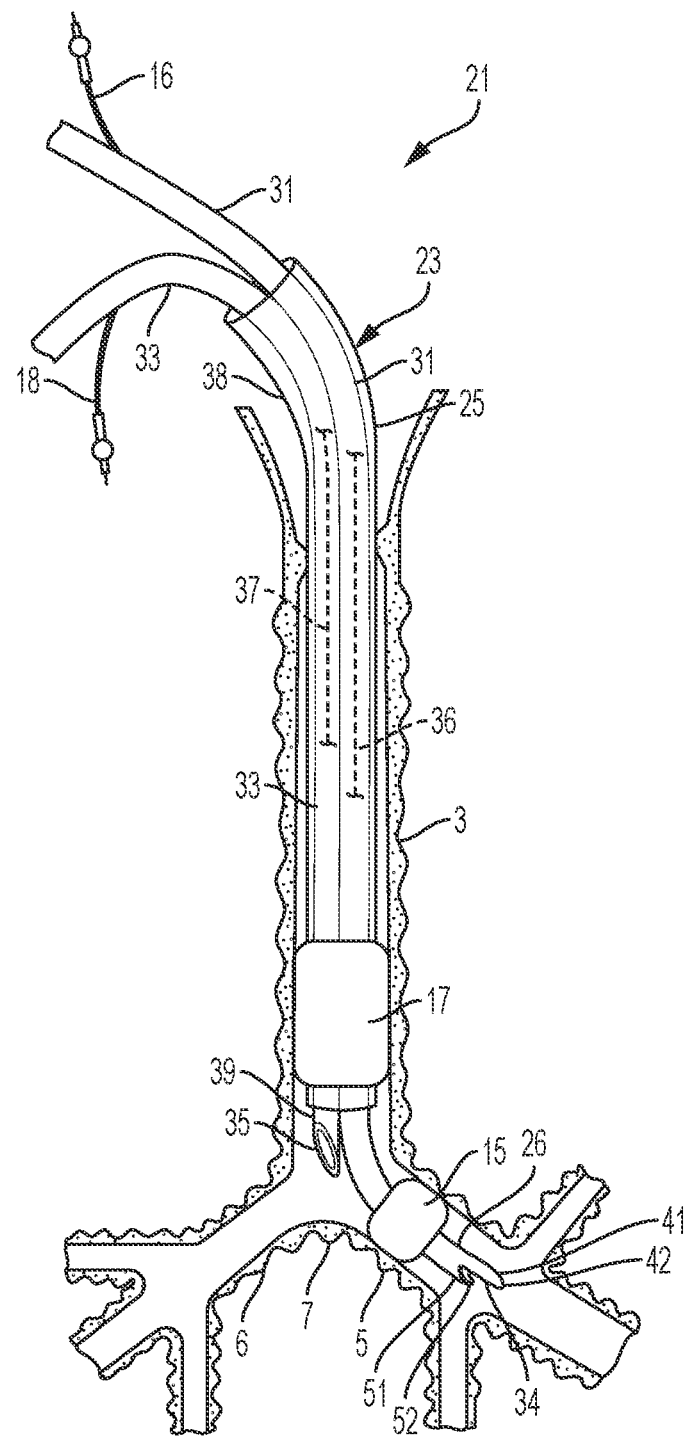
FIG. 7 schematically illustrates a double lumen endotracheal device in relation to the trachea, right bronchia, and left bronchia.

FIGS. 3, 5, and 7 further disclose the endotracheal device 21 having an inflatable cuff 15 on the distal portion 26 of the lumen, such as the bronchial lumen 31, an inflation line 16 for the inflatable cuff 15, and a tube member 23 that at least partially surrounds the bronchial lumen 31. Moreover, referring to FIGS. 5 and 7, FIGS. 5 and 7 further discloses an inflatable cuff 17 on the distal portion 26 of the bronchial lumen 31 and distal portion 39 of a second lumen 33 such as the tracheal lumen, an inflation line 18 for the inflatable cuff 17, and whereby the tube member 23 at least partially surrounds the lumen 31.

Referring to FIG. 7, FIG. 7 schematically illustrates the endotracheal device 21 in relation to the trachea 3, right bronchia 6, left bronchia 5, and tracheal carina 7.

Figure 4:
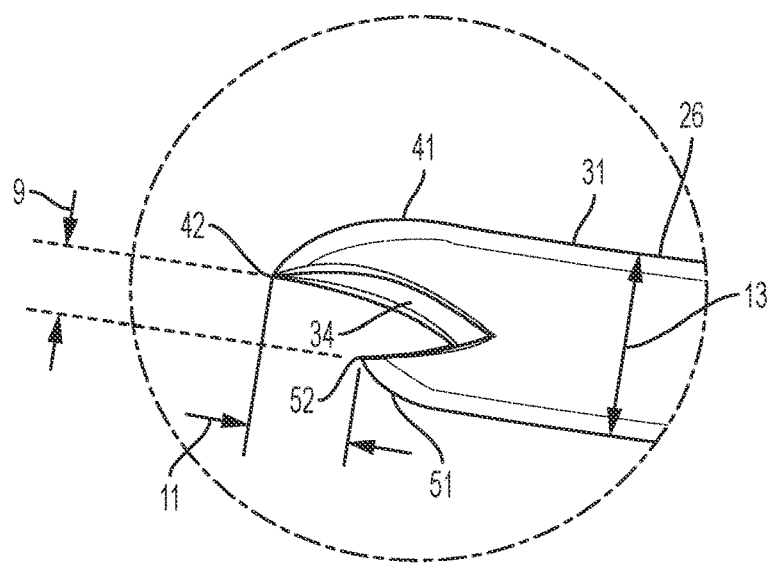
FIG. 4 schematically illustrates an enlarged partial view of the single lumen endotracheal device of FIG. 3.

FIG. 4 schematically illustrates an enlarged partial view of the single lumen endotracheal device of FIG. 3 (as discussed above pertaining to FIG. 3).

Figure 6:
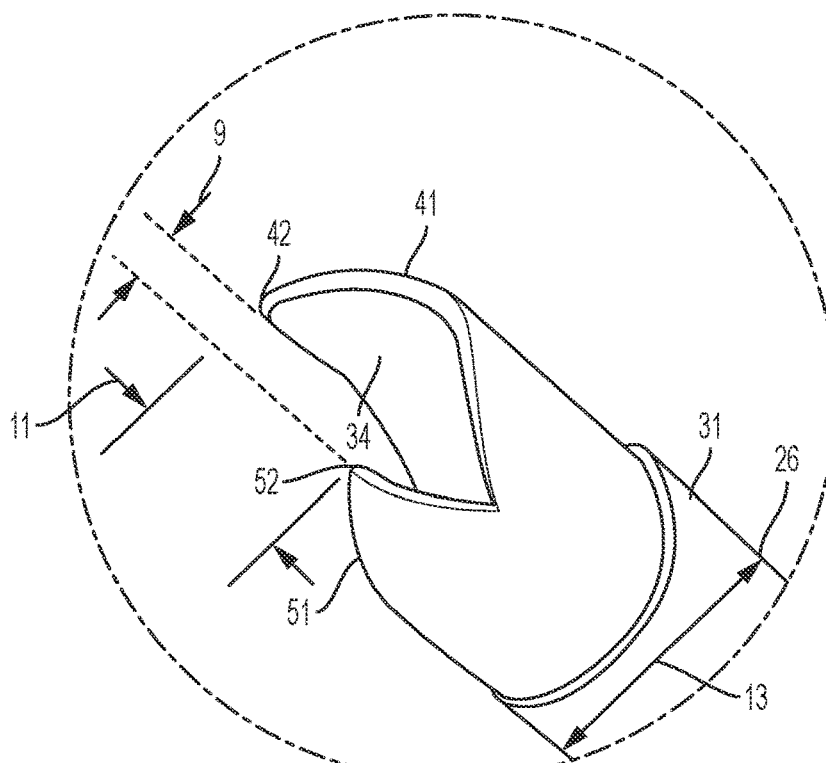
FIG. 6 schematically illustrates an enlarged partial view of the double lumen endotracheal device of FIG. 5.

FIG. 6 schematically illustrates an enlarged partial view of the double lumen endotracheal device of FIG. 5 (as discussed above pertaining to FIG. 5).

Figure 9:
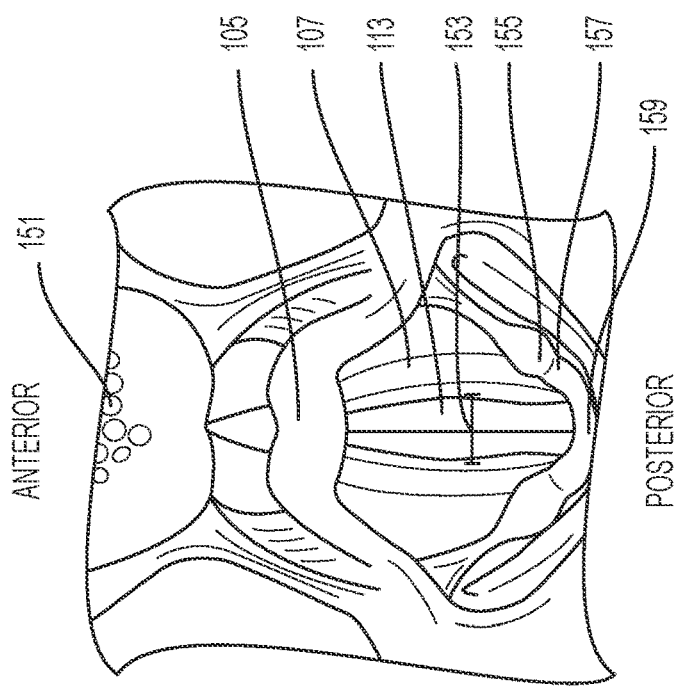
FIG. 9 schematically illustrates a laryngoscopic view depiction of a human subject revealing the glottis in the closed position.

FIG. 9 schematically illustrates a laryngoscopic view depiction of a human subject revealing the glottis 153 in the closed position.

Figure 10:
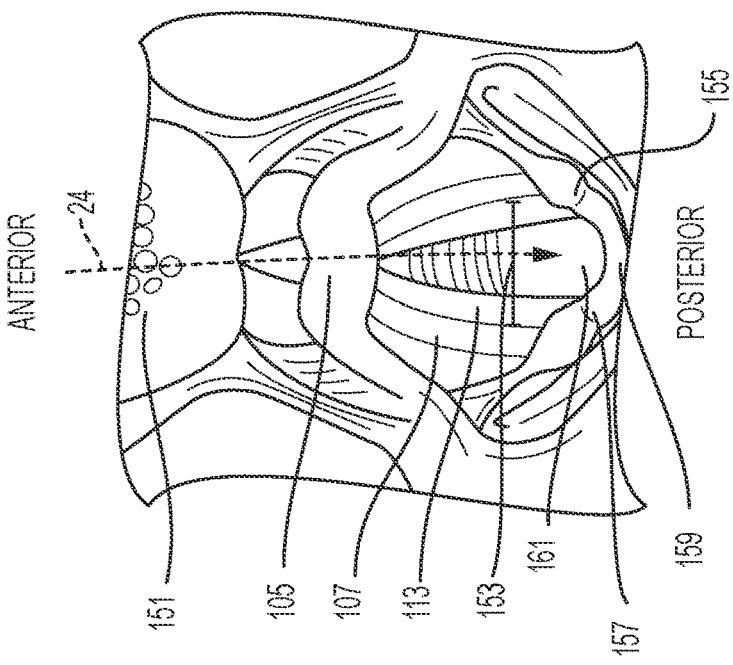
FIG. 10 schematically illustrates a laryngoscopic view depiction of a human subject revealing the glottis in the open position with an associated path of an endotracheal device.

FIG. 10 schematically illustrates a laryngoscopic view depiction of a human subject revealing the glottis 153 in the open position, and with an associated path 24 of an endotracheal device.

In FIGS. 9 and 10, also depicted are the base of tongue 151, epiglottis 105, ventricular fold ("false vocal cord") 107, vocal cord ("true vocal cord") 113, glottis 153, corniculate cartilage 155, arytenoid tissue 157, interarytenoid tissue 159, and inner lining of trachea 161.

Figure 8:
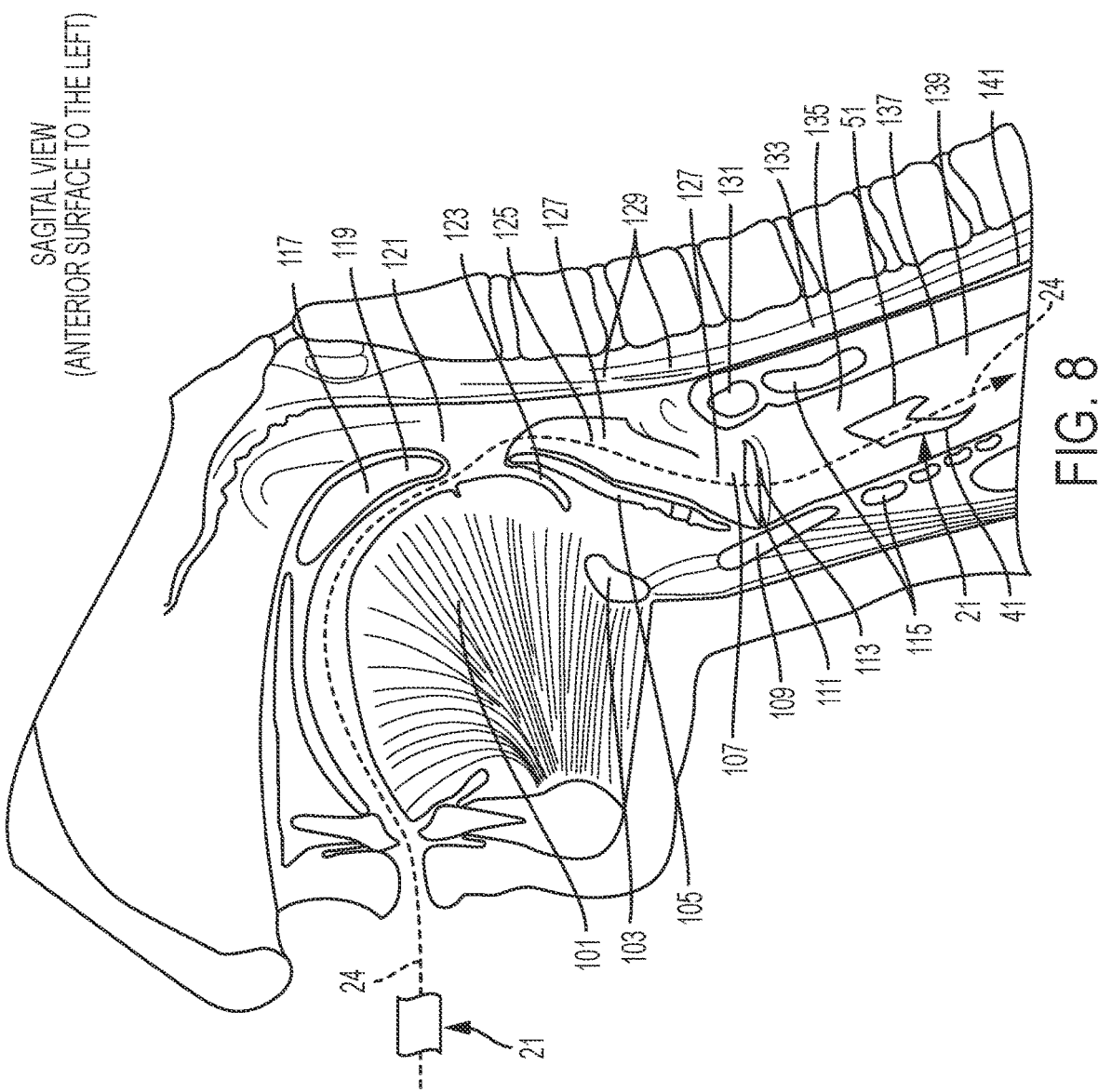
FIG. 8 schematically illustrates a sagittal section depiction of a head and neck of a human subject (anterior surface to the left) with segments of an endotracheal tube and its associated path.

FIG. 8 schematically illustrates a sagittal section depiction of a head and neck of a human subject (anterior surface to the left) with segments of an endotracheal device 21 revealing the anterior beak 41, posterior beak 51, and an associated path 24 of the endotracheal device 21. The associated path 24 of the endotracheal device 21 may extend deeper or shallower within the tracheobronchial tree than as illustrated.

Figure 11:
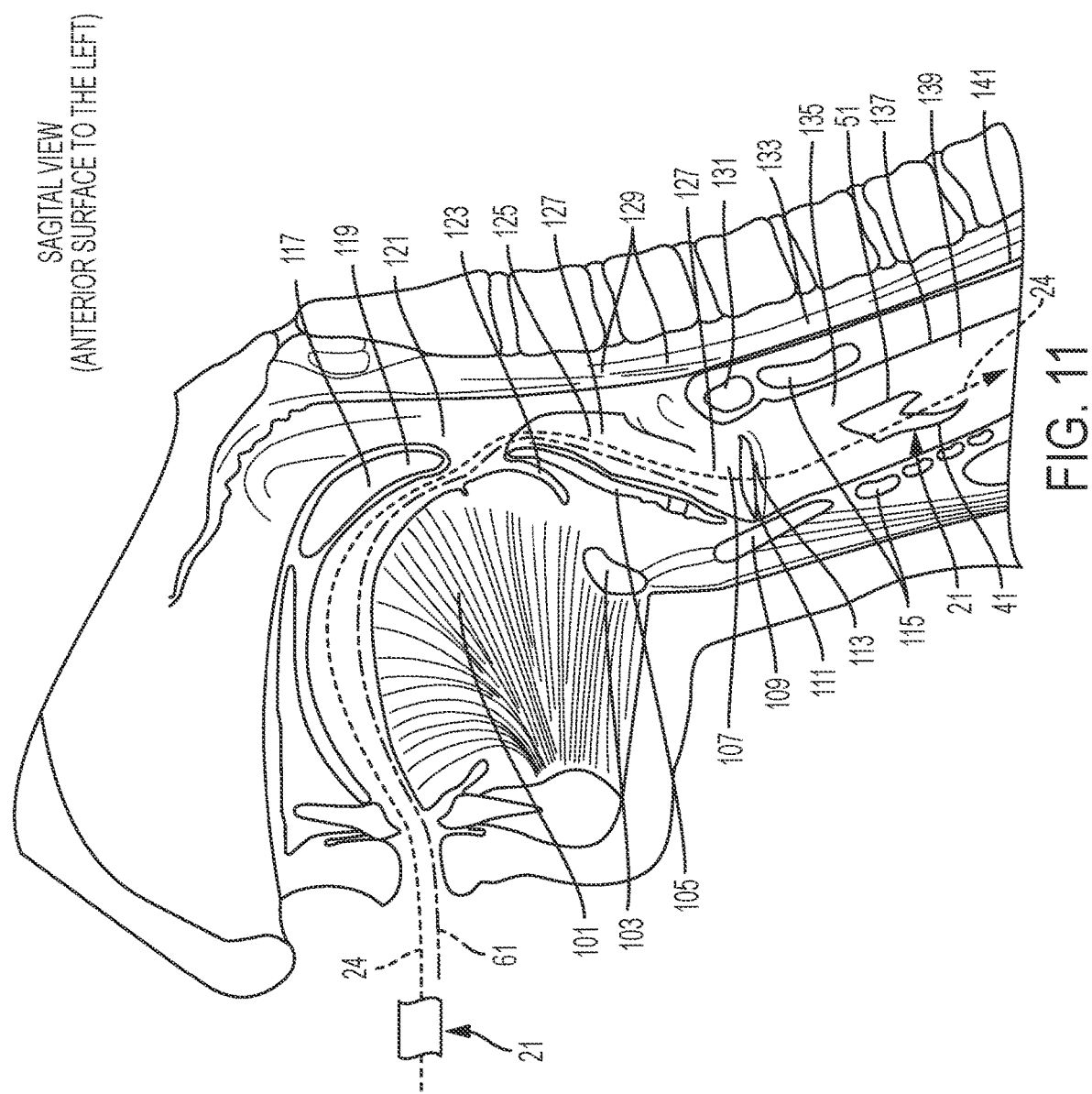
FIG. 11 schematically illustrates a sagittal section depiction of a head and neck of a human subject (anterior surface to the left) with segments of an endotracheal tube and its associated path and an associated path of a medical device or instrument.

In FIGS. 8 and 11, also depicted are the tongue 101, hyoid bone 103, epiglottis 105, ventricular fold ("false vocal cord") 107, thyroid cartilage 109, ventricle 111, vocal fold ("true vocal cord") 113, cricoid cartilage 115, pharyngeal palate 117, uvula 119, junction of mouth and pharynx 121, vallecula 123, laryngeal aditus 125, vestibule 127, posterior pharyngeal wall 129, interarytenoideus 131, cricopharyngeus 133, subglottic trachea 135, posterior of trachea wall 137, trachea 139, and esophagus 141.

FIG. 11 schematically illustrates a sagittal section depiction of a head and neck of a human subject (anterior surface to the left) with segments of an endotracheal device 21 revealing the anterior beak 41, posterior beak 51, and an associated path 24 of the endotracheal device 21. Moreover, FIG. 10 schematically illustrates an associated path 61 of a medical device or instrument (specific device or instrument not shown). The medical device or instrument may be an introducing device, for example. An introducing device may include, but not limited thereto, fiberoptic bronchoscopes, airway exchange catheters, endotracheal tube introducers, obturator/wire devices, or the like. The associated path 61 of the medical device or instrument may extend deeper or shallower within the tracheobronchial tree than as illustrated. The associated path 24 of the endotracheal device 21 may extend deeper or shallower within the tracheobronchial tree than as illustrated.

The endotracheal device may be used with an image recording device (such as a camera, video recording or other imaging means) as well as other devices and surgical and medical instruments. The acquired image or related data may be communicated locally and/or remotely to the surgeon, clinician, user, and/or processor. Similarly, any data or information acquired by the components, equipment, or instruments associated with the endotracheal device may be communicated locally and/or remotely to the surgeon, clinician, user, and/or processor.

The various components of the endotracheal device as well as other medical instruments and devices may be a variety of materials such as, but not limited thereto, plastic, metal, polyvinyl chloride (PVC), silicone, stainless steel, polycarbonate, nylon, polymers, acetal polymers, ceramics, etc.

In an embodiment the exterior wall of the anterior beak is generally bent or curved inward having a rounded shape and the exterior wall of the posterior beak is generally bent or curved inward having a rounded shape. The anterior beak is defined whereby its exterior wall is generally bent or curved inward having a rounded shape. The posterior beak is defined whereby its exterior wall is generally bent or curved inward having a rounded shape. In an embodiment only one of the anterior beak or posterior beak is generally bent inward. In an embodiment more than an anterior beak and posterior beak may be implemented (i.e., three or more beaks as desired or required). For example, three or more beaks may be implemented whereby the multiple beaks are arranged circumferentially along the end of the lumen of the endotracheal device. In an embodiment, the anterior beak and posterior beak may be circumferentially opposite to one another. In an embodiment, the anterior beak and posterior beak may be circumferentially staggered so as not to be precisely aligned directly opposite. In an embodiment one or two lumens may be implemented for the endotracheal device. In an embodiment greater than (or equal to) two lumens may be implemented for the endotracheal device; and arranged side-by-side, coaxially, or a combination thereof. In an embodiment the multiple beak elements may be included on other medical devices or instruments other than endotracheal tubes.

EXAMPLES

Practice of an aspect of an embodiment (or embodiments) of the invention will be still more fully understood from the following examples and experimental results, which are presented herein for illustration only and should not be construed as limiting the invention in any way.

Example 1. An endotracheal device, said device comprising: a lumen having an inner diameter and central axis running longitudinally along the length of the lumen; said lumen having a proximal portion and a distal portion opposite said proximal portion; and said distal portion having an anterior beak that includes a distal tip of the anterior beak and a posterior beak having a distal tip of the posterior beak.

Example 2. The endotracheal device of example 1, wherein: said distal tip of said anterior beak longitudinally extends distally a predetermined distance from said distal tip of said posterior beak so as to define a longitudinal beak offset.

Example 3. The endotracheal device of example 2, wherein: said distal tip of said anterior beak is laterally inward a predetermined distance from said distal tip of said posterior beak so as to define a lateral-inward beak offset.

Example 4. The endotracheal device of example 1 (as well as subject matter in whole or in part of example 3), wherein: said distal tip of said anterior beak is laterally inward a predetermined distance from said distal tip of said posterior beak so as to define a lateral-inward beak offset.

Example 5. The endotracheal device of example 3 (as well as subject matter in whole or in part of example 4), wherein said longitudinal beak offset is equal to about said inner diameter of said lumen.

Example 6. The endotracheal device of example 3 (as well as subject matter of one or more of any combination of examples 4-5, in whole or in part), wherein said longitudinal beak offset is equal to about forty percent of said inner diameter of said lumen.

Example 7. The endotracheal device of example 3 (as well as subject matter of one or more of any combination of examples 4-6, in whole or in part), wherein said longitudinal beak offset is in the range of one of the following:
   about 45 percent to about 50 percent of said inner diameter of said lumen;
   about 50 percent to about 55 percent of said inner diameter of said lumen;
   about 55 percent to about 60 percent of said inner diameter of said lumen;
   about 60 percent to about 65 percent of said inner diameter of said lumen;
   about 65 percent to about 70 percent of said inner diameter of said lumen;
   about 70 percent to about 75 percent of said inner diameter of said lumen;
   about 75 percent to about 80 percent of said inner diameter of said lumen;
   about 80 percent to about 85 percent of said inner diameter of said lumen;
   about 85 percent to about 90 percent of said inner diameter of said lumen;
   about 90 percent to about 95 percent of said inner diameter of said lumen; or about 95 percent to about 100 percent of said inner diameter of said lumen.

Example 8. The endotracheal device of example 3 (as well as subject matter of one or more of any combination of examples 4-7, in whole or in part), wherein said longitudinal beak offset is equal to about thirty percent of said inner diameter of said lumen or 120 percent of said inner diameter of said lumen. In an embodiment the longitudinal beak offset may be greater than 120 percent of said inner diameter of said lumen, such as less than or equal to double said inner diameter of said lumen.

Example 9. The endotracheal device of example 1 (as well as subject matter of one or more of any combination of examples 2-8, in whole or in part), further comprising a medical device or instrument to be used in a medical kit.

Example 10. The endotracheal device of example 1 (as well as subject matter of one or more of any combination of examples 2-9, in whole or in part), wherein said medical device or instrument includes any combination of one or more of the following: fiberoptic bronchoscope, airway exchange catheter, endotracheal tube introducer, and obturator/wire device.

Example 11. The endotracheal device of example 1 (as well as subject matter of one or more of any combination of examples 2-10, in whole or in part), wherein: said lumen is configured to longitudinally traverse exterior along a medical device or instrument.

Example 12. The endotracheal device of example 1 (as well as subject matter of one or more of any combination of examples 2-11, in whole or in part), wherein: said lumen is configured to longitudinally traverse coaxially inside a medical device or instrument.

Example 13. The endotracheal device of example 1 (as well as subject matter of one or more of any combination of examples 2-12, in whole or in part), wherein: said lumen is configured to longitudinally traverse coaxially outside a medical device or instrument.

Example 14. The endotracheal device of anyone of examples 11, 12, or 13 (as well as subject matter of one or more of any combination of examples 2-13, in whole or in part), wherein said medical device or instrument comprises at least one of any combination of the following: fiberoptic bronchoscope, airway exchange catheter, endotracheal tube introducer, or and obturator/wire.

Example 15. The endotracheal device of example 3 (as well as subject matter of one or more of any combination of examples 4-14, in whole or in part), wherein said lateral-inward beak offset is equal to about said inner diameter of said lumen.

Example 16. The endotracheal device of example 3 (as well as subject matter of one or more of any combination of examples 4-15, in whole or in part), wherein said lateral-inward beak offset is equal to about seventy-five percent of said inner diameter of said lumen.

Example 17. The endotracheal device of example 3 (as well as subject matter of one or more of any combination of examples 4-16, in whole or in part), wherein said lateral-inward beak offset is equal to about 50 percent to about ninety percent of said diameter of said inner lumen.

Example 18. The endotracheal device of example 3 (as well as subject matter of one or more of any combination of examples 4-17, in whole or in part), wherein said lateral-inward beak offset is zero.

Example 19. The endotracheal device of example 3 (as well as subject matter of one or more of any combination of examples 4-18, in whole or in part), wherein said lateral-inward beak offset is in the range of one of the following:
   about 50 percent to about 55 percent of said inner diameter of said lumen;
   about 55 percent to about 60 percent of said inner diameter of said lumen;
   about 60 percent to about 65 percent of said inner diameter of said lumen;
   about 65 percent to about 70 percent of said inner diameter of said lumen;
   about 70 percent to about 75 percent of said inner diameter of said lumen;
   about 75 percent to about 80 percent of said inner diameter of said lumen;
   about 80 percent to about 85 percent of said inner diameter of said lumen;
   about 85 percent to about 90 percent of said inner diameter of said lumen;
   about 90 percent to about 95 percent of said inner diameter of said lumen; or about 95 percent to about 100 percent of said inner diameter of said lumen.

Example 20. The endotracheal device of example 2 (as well as subject matter of one or more of any combination of examples 3-19, in whole or in part), wherein: said distal tip of said anterior beak is laterally outward a predetermined distance from said distal tip of said posterior beak so as to define a lateral-outward beak offset.

Example 21. The endotracheal device of example 1 (as well as subject matter of one or more of any combination of examples 2-20, in whole or in part), wherein: said distal tip of said anterior beak is laterally outward a predetermined distance from said distal tip of said posterior beak so as to define a lateral-outward beak offset. In an embodiment the lateral-outward beak offset may be in ranges of about 1 percent, 10 percent, 20 percent, 30 percent, 40 percent, 50 percent, 60 percent, 70 percent, 80 percent, 90 percent, or 100 percent (or any levels in between said aforementioned list of percentages) of said diameter of said inner lumen.

Example 22. The method of using any of the devices, systems, apparatuses, assemblies, or their components provided in any one or more of examples 1-21.

Example 23. The method of providing instructions to use or operate of any of the devices, systems, apparatuses, assemblies, or their components provided in any one or more of examples 1-21.

Example 24. The method of manufacturing any of the devices, systems, apparatuses, assemblies, or their components provided in any one or more of examples 1-21.

Example 25. A method and an apparatus (as well as subject matter of one or more of any combination of examples 1-21, in whole or in part) for inserting an endotracheal device and/or medical device or instrument into the location of interest of the site of the subject Example 26. A method and device (as well as subject matter of one or more of any combination of examples 1-21, in whole or in part) for performing endotracheal intubation on a subject Example 27. It is noted that machine readable medium or computer useable medium may be configured to execute the subject matter pertaining to the device (e.g., system or apparatus) or related methods disclosed in examples 1-21, as well as examples 22-26.

Example 28. An endotracheal device, said device comprising:
a lumen having an inner diameter and central axis running longitudinally along the length of the lumen;
said lumen having a proximal portion and a distal portion opposite said proximal portion; and
said distal portion having an anterior beak that includes a distal tip of the anterior beak and a posterior beak having a distal tip of the posterior beak
said anterior beak having an exterior wall whereby said exterior wall has a configuration that is generally curved inward having a rounded shape;
said posterior beak having an exterior wall whereby said exterior wall has a configuration that is generally curved inward having a rounded shape;
said distal tip of said anterior beak longitudinally extends distally at a predetermined distance distally from said distal tip of said posterior beak so as to define a longitudinal beak offset; and
said distal tip of said anterior beak and said distal tip of said posterior beak are configured laterally inward toward one another at a predetermined distance laterally from each other so as to define a lateral-inward beak offset.

Example 29. The endotracheal device of example 28, wherein said longitudinal beak offset is equal to about said inner diameter of said lumen.

Example 30. The endotracheal device of example 28, wherein said longitudinal beak offset is equal to about forty percent of said inner diameter of said lumen.

Example 31. The endotracheal device of example 28, wherein said longitudinal beak offset is in the range of one of the following:
about 45 percent to about 50 percent of said inner diameter of said lumen;
about 50 percent to about 55 percent of said inner diameter of said lumen;
about 55 percent to about 60 percent of said inner diameter of said lumen;
about 60 percent to about 65 percent of said inner diameter of said lumen;
about 65 percent to about 70 percent of said inner diameter of said lumen;
about 70 percent to about 75 percent of said inner diameter of said lumen;
about 75 percent to about 80 percent of said inner diameter of said lumen;
about 80 percent to about 85 percent of said inner diameter of said lumen;
about 85 percent to about 90 percent of said inner diameter of said lumen;
about 90 percent to about 95 percent of said inner diameter of said lumen; or about 95 percent to about 100 percent of said inner diameter of said lumen.

Example 32. The endotracheal device of example 28, wherein said longitudinal beak offset is equal to about thirty percent of said inner diameter of said lumen or 120 percent of said inner diameter of said lumen.

Example 33. The endotracheal device of example 28, further comprising a medical device or instrument to be used in a medical kit.

Example 34. The endotracheal device of example 33, wherein said medical device or instrument includes any combination of one or more of the following: fiberoptic bronchoscope, airway exchange catheter, endotracheal tube introducer, and obturator/wire device.

Example 35. The endotracheal device of example 28, wherein:
said lumen is configured to longitudinally traverse exterior along a medical device or instrument.

Example 36. The endotracheal device of example 28, wherein:
said lumen is configured to longitudinally traverse coaxially inside a medical device or instrument.

Example 37. The endotracheal device of example 28, wherein:
said lumen is configured to longitudinally traverse coaxially outside a medical device or instrument.

Example 38. The endotracheal device of example 35, wherein said medical device or instrument comprises at least one of any combination of the following:
fiberoptic bronchoscope, airway exchange catheter, endotracheal tube introducer, or and obturator/wire.

Example 39. The endotracheal device of example 28, wherein said lateral-inward beak offset is equal to about said inner diameter of said lumen.

Example 40. The endotracheal device of example 28, wherein said lateral-inward beak offset is equal to about seventy-five percent of said inner diameter of said lumen.

Example 41. The endotracheal device of example 28, wherein said lateral-inward beak offset is equal to about 50 percent to about ninety percent of said inner diameter of said lumen.

Example 42. The endotracheal device of example 28, wherein said longitudinal beak offset is equal to about thirty percent to 200 percent of said inner diameter of said lumen.

Example 43. The endotracheal device of example 28, wherein said lateral-inward beak offset is in the range of one of the following:
about 50 percent to about 55 percent of said inner diameter of said lumen;
about 55 percent to about 60 percent of said inner diameter of said lumen;
about 60 percent to about 65 percent of said inner diameter of said lumen;
about 65 percent to about 70 percent of said inner diameter of said lumen;
about 70 percent to about 75 percent of said inner diameter of said lumen;
about 75 percent to about 80 percent of said inner diameter of said lumen;
about 80 percent to about 85 percent of said inner diameter of said lumen;
about 85 percent to about 90 percent of said inner diameter of said lumen;
about 90 percent to about 95 percent of said inner diameter of said lumen; or about 95 percent said inner diameter of said lumen but less than 100 percent of said inner diameter of said lumen.

Example 44. The endotracheal device of example 36, wherein said medical device or instrument comprises at least one of any combination of the following:
fiberoptic bronchoscope, airway exchange catheter, endotracheal tube introducer, or and obturator/wire.

Example 45. The endotracheal device of example 37, wherein said medical device or instrument comprises at least one of any combination of the following:
fiberoptic bronchoscope, airway exchange catheter, endotracheal tube introducer, or and obturator/wire.

Example 46. The endotracheal device of example 28, wherein said device comprises a material selected from one of the following:
plastic, metal, polyvinyl chloride (PVC), silicone, stainless steel, polycarbonate, nylon, polymers, acetal polymers, or ceramics.

Example 47. The endotracheal device of any one of examples 28, 29-37, 39-43, and 46, wherein said device further comprises:
a second lumen having an inner diameter and central axis running longitudinally along the length of the second lumen and said second lumen is positioned adjacent to said first lumen;
said lumen having a proximal portion and a distal portion opposite said proximal portion; and
said second lumen having an aperture at said distal portion.

REFERENCES

The devices, systems, apparatuses, compositions, materials, machine readable medium, computer program products, and methods of various embodiments of the invention disclosed herein may utilize aspects disclosed in the following references, applications, publications and patents and which are hereby incorporated by reference herein in their entirety, and which are not admitted to be prior art with respect to the present invention by inclusion in this section:
1. U.S. Pat. No. 6,609,521 B1, Belani, K., et al., "Endotracheal Tube", Aug. 26, 2003.
2. U.S. Pat. No. 5,873,362, Parker, J., "Endotracheal Tube", Feb. 23, 1999.
3. U.S. Patent Application Publication No. US 2010/0113916 A1, Kumar, A., "Systems and Methods for Endotracheal Tube Positioning", May 6, 2010.
4. U.S. Pat. No. 6,568,393 B2, Christopher, K., "Endotracheal Tube Having a Beveled Tip and Orientation Indicator", May 27, 2003.
5. U.S. Pat. No. 6,698,428 B2, Brain, A., "Endotracheal Tube Construction", Mar. 2, 2004.
6. U.S. Pat. No. 6,918,391 B1, Moore, J., "Multi-Lumen Endotracheal Tube", Jul. 19, 2005.
7. U.S. Patent Application Publication No. US 2008/0216839 A1, Rutter, M., Sep. 11, 2008.
8. U.S. Pat. No. 5,339,805 A, Parker, J. D., "Blind Orolaryngeal and Oroesophageal Guiding and Aiming Device", Aug. 23, 1994.
9. U.S. Pat. No. 5,845,634 A, Parker, J. D., "Endoscope Viewing System with Orotracheal Introducing Guide", Dec. 8, 1998.
10. U.S. Pat. No. 5,743,254 A, Parker, J. D., "Orotracheal Intubation Guide", Apr. 28, 1998.
11. U.S. Pat. No. 6,672,305 B2, Parker, J. D., "Shallow Throat Orotracheal Intubation Guide", Jan. 6, 2004.
12. U.S. Pat. No. 7,174,889 B2, Boedeker, B., et al., "Device for Insertion of Endotracheal Tube", Feb. 13, 2007.
13. U.S. Patent Application Publication No. US 2010/0224186 A1, Uesugi, T., "Endotracheal Intubation Assist Instrument", Sep. 9, 2010.
14. Johnson, Dana M., et al., "Endoscopic Study of Mechanism of Failure of Endotracheal Tube Advancement into the Trachea during Awake Fiberoptic Orotracheal Intubation", Anesthesiology, V 102, No. 5, May 2005, pages 910-914.
15. Maktabi, Mazen, A., et al., "Laryngeal Trauma during Awake Fiberoptic Intubation", Anesth. Analg. 2002, 95, pages 1112-4.

Unless clearly specified to the contrary, there is no requirement for any particular described or illustrated activity or element, any particular sequence or such activities, any particular size, speed, material, duration, contour, dimension or frequency, or any particularly interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. It should be appreciated that aspects of the present invention may have a variety of sizes, contours, shapes, compositions and materials as desired or required.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

I claim:

1. An endotracheal device, said device comprising:
   a lumen having an inner diameter and central axis running longitudinally along the length of the lumen;
   said lumen having a proximal portion and a distal portion opposite said proximal portion;
   said distal portion having an anterior beak that includes a distal tip of the anterior beak and a posterior beak having a distal tip of the posterior beak;
   said anterior beak having an exterior wall whereby said exterior wall has a configuration that is generally curved inward having a rounded shape;
   said posterior beak having an exterior wall whereby said exterior wall has a configuration that is generally curved inward having a rounded shape;
   said distal tip of said anterior beak is longitudinally spaced at a predetermined distance distally from said distal tip of said posterior beak so as to define a longitudinal beak offset;
   said distal tip of said anterior beak and said distal tip of said posterior beak are configured laterally inward toward one another and spaced at a predetermined distance laterally from each other in a relaxed state so as to define a lateral-inward beak offset; and
   wherein said lateral-inward beak offset is in the range of about 50 percent to 90 percent of said inner diameter of said lumen.

2. The endotracheal device of claim 1, wherein said longitudinal beak offset is one of the following:
   equal to about said inner diameter of said lumen;
   equal to about forty percent of said inner diameter of said lumen;
   in the range of about 45 percent to 50 percent of said inner diameter of said lumen;
   in the range of 50 percent to 55 percent of said inner diameter of said lumen;
   in the range of 55 percent to 60 percent of said inner diameter of said lumen;
   in the range of 60 percent to 65 percent of said inner diameter of said lumen;
   in the range of 65 percent to 70 percent of said inner diameter of said lumen;
   in the range of 70 percent to 75 percent of said inner diameter of said lumen;
   in the range of 75 percent to 80 percent of said inner diameter of said lumen;
   in the range of 80 percent to 85 percent of said inner diameter of said lumen;
   in the range of 85 percent to 90 percent of said inner diameter of said lumen;
   in the range of 90 percent to 95 percent of said inner diameter of said lumen;
   in the range of 95 percent to 100 percent of said inner diameter of said lumen;
   in the range of about 30 percent to about 120 percent of said inner diameter of said lumen; or
   in the range of about to 30 percent to 200 percent of said inner diameter of said lumen.

3. The endotracheal device of claim 1, further comprising a medical device or instrument to be used in a medical kit.

4. The endotracheal device of claim 3, wherein said medical device or instrument includes one or more of the following: fiberoptic bronchoscope, airway exchange catheter, endotracheal tube introducer, or obturator/wire device.

5. The endotracheal device of claim 1, wherein:
   said lumen is configured to longitudinally traverse exterior along a medical device or instrument.

6. The endotracheal device of claim 5, wherein said medical device or instrument comprises at least one of the following:
   fiberoptic bronchoscope, airway exchange catheter, endotracheal tube introducer, or obturator/wire.

7. The endotracheal device of claim 1, wherein:
   said lumen is configured to longitudinally traverse coaxially inside a medical device or instrument.

8. The endotracheal device of claim 7, wherein said medical device or instrument comprises at least one of the following:
   fiberoptic bronchoscope, airway exchange catheter, endotracheal tube introducer, or obturator/wire.

9. The endotracheal device of claim 1, wherein:
   said lumen is configured to longitudinally traverse coaxially outside a medical device or instrument.

10. The endotracheal device of claim 9, wherein said medical device or instrument comprises at least one of the following:
    fiberoptic bronchoscope, airway exchange catheter, endotracheal tube introducer, or obturator/wire.

11. The endotracheal device of claim 1, wherein said device comprises a material selected from one of the following:
    plastic, metal, polyvinyl chloride (PVC), silicone, stainless steel, polycarbonate, nylon, polymers, acetal polymers, or ceramics.

12. The endotracheal device of any one of claims 1, 2, 3-9, and 11, wherein said device further comprises:

a second lumen having an inner diameter and central axis running longitudinally along the length of the second lumen and said second lumen is positioned adjacent to said first lumen;
said lumen having a proximal portion and a distal portion opposite said proximal portion; and
said second lumen having an aperture at said distal portion.

13. An endotracheal device, said device comprising:
a lumen having an inner diameter and central axis running longitudinally along the length of the lumen;
said lumen having a proximal portion and a distal portion opposite said proximal portion;
said distal portion having an anterior beak that includes a distal tip of the anterior beak and a posterior beak having a distal tip of the posterior beak;
said anterior beak having an exterior wall whereby said exterior wall has a configuration that is generally curved inward having a rounded shape;
said posterior beak having an exterior wall whereby said exterior wall has a configuration that is generally curved inward having a rounded shape;
said distal tip of said anterior beak is longitudinally spaced at a predetermined distance distally from said distal tip of said posterior beak so as to define a longitudinal beak offset;
said distal tip of said anterior beak and said distal tip of said posterior beak are configured laterally inward toward one another and spaced at a predetermined distance laterally from each other in a relaxed state so as to define a lateral-inward beak offset; and
wherein said longitudinal beak offset is one of the following:
equal to said inner diameter of said lumen;
equal to forty percent of said inner diameter of said lumen;
in the range of 45 percent to 50 percent of said inner diameter of said lumen;
in the range of 50 percent to 55 percent of said inner diameter of said lumen;
in the range of 55 percent to 60 percent of said inner diameter of said lumen;
in the range of 60 percent to 65 percent of said inner diameter of said lumen;
in the range of 65 percent to 70 percent of said inner diameter of said lumen;
in the range of 70 percent to 75 percent of said inner diameter of said lumen;
in the range of 75 percent to 80 percent of said inner diameter of said lumen;
in the range of 80 percent to 85 percent of said inner diameter of said lumen;
in the range of 85 percent to 90 percent of said inner diameter of said lumen;
in the range of 90 percent to 95 percent of said inner diameter of said lumen;
in the range of 95 percent to 100 percent of said inner diameter of said lumen;
in the range of about 30 percent to about 120 percent of said inner diameter of said lumen; or
in the range of about 30 percent to 200 percent of said inner diameter of said lumen.

14. The endotracheal device of claim 13, further comprising a medical device or instrument to be used in a medical kit.

15. The endotracheal device of claim 14, wherein said medical device or instrument includes one or more of the following: fiberoptic bronchoscope, airway exchange catheter, endotracheal tube introducer, or obturator/wire device.

16. The endotracheal device of claim 13, wherein:
said lumen is configured to longitudinally traverse exterior along a medical device or instrument.

17. The endotracheal device of claim 16, wherein said medical device or instrument comprises at least one of the following:
fiberoptic bronchoscope, airway exchange catheter, endotracheal tube introducer, or obturator/wire.

18. The endotracheal device of claim 13, wherein:
said lumen is configured to longitudinally traverse coaxially inside a medical device or instrument.

19. The endotracheal device of claim 18, wherein said medical device or instrument comprises at least one of the following:
fiberoptic bronchoscope, airway exchange catheter, endotracheal tube introducer, or obturator/wire.

20. The endotracheal device of claim 13, wherein:
said lumen is configured to longitudinally traverse coaxially outside a medical device or instrument.

21. The endotracheal device of claim 20, wherein said medical device or instrument comprises at least one of the following:
fiberoptic bronchoscope, airway exchange catheter, endotracheal tube introducer, or obturator/wire.

22. The endotracheal device of claim 13, wherein said lateral-inward beak offset is in the range of one of the following:
about 50 percent to 55 percent of said inner diameter of said lumen;
55 percent to 60 percent of said inner diameter of said lumen;
60 percent to 65 percent of said inner diameter of said lumen;
65 percent to 70 percent of said inner diameter of said lumen;
70 percent to 75 percent of said inner diameter of said lumen;
75 percent to 80 percent of said inner diameter of said lumen;
80 percent to 85 percent of said inner diameter of said lumen;
85 percent to 90 percent of said inner diameter of said lumen; or
90 percent to 95 percent of said inner diameter of said lumen.

23. The endotracheal device of claim 13, wherein said device comprises a material selected from one of the following:
plastic, metal, polyvinyl chloride (PVC), silicone, stainless steel, polycarbonate, nylon, polymers, acetal polymers, or ceramics.

24. The endotracheal device of any one of claims 13-20, 22, and 23, wherein said device further comprises:
a second lumen having an inner diameter and central axis running longitudinally along the length of the second lumen and said second lumen is positioned adjacent to said first lumen;
said lumen having a proximal portion and a distal portion opposite said proximal portion; and
said second lumen having an aperture at said distal portion.

* * * * *